United States Patent [19]

Chu et al.

[11] Patent Number: 5,717,778
[45] Date of Patent: Feb. 10, 1998

[54] OPTICAL SPECIMEN ANALYSIS SYSTEM AND METHOD

[76] Inventors: Albert E. Chu, 140 Roblar Ave., Hillsborough, Calif. 94010; Lian Tao, 2223 27th Ave., San Francisco, Calif. 94116

[21] Appl. No.: 465,089

[22] Filed: Jun. 5, 1995

Related U.S. Application Data

[63] Continuation-in-part of Ser. No. 23,113, Feb. 26, 1993, abandoned.

[51] Int. Cl.$^6$ .................................................. G06K 9/00
[52] U.S. Cl. ........................................ 382/133; 382/274
[58] Field of Search .................................. 382/110, 128, 382/129, 130, 133, 134, 162, 164, 165, 173, 175, 180, 181, 190, 224, 274, 287, 300, 321; 436/43, 538, 164, 805, 807, 544, 536; 422/67, 73, 82.05, 82.08, 82.09, 56, 57; 352/213; 356/23, 246, 39; 364/413.13

[56] References Cited

U.S. PATENT DOCUMENTS

| | | | |
|---|---|---|---|
| 4,097,845 | 6/1978 | Bacus | 382/6 |
| 4,335,427 | 6/1982 | Hunt et al. | 364/414 |
| 4,338,024 | 7/1982 | Bolz et al. | 356/23 |
| 4,404,289 | 9/1983 | Masuda et al. | 436/538 |
| 4,476,231 | 10/1984 | Deindoerfer et al. | 382/6 |
| 4,537,861 | 8/1985 | Elings et al. | 436/518 |
| 4,538,227 | 8/1985 | Toraichi et al. | 364/414 |
| 4,563,701 | 1/1986 | Gilath | 358/111 |
| 4,590,582 | 5/1986 | Umemura | 364/724 |
| 4,611,340 | 9/1986 | Okazaki | 378/95 |
| 4,647,544 | 3/1987 | Nicoli et al. | 436/518 |
| 4,648,053 | 3/1987 | Fridge | 364/551 |
| 4,674,108 | 6/1987 | Asahina et al. | 378/99 |
| 4,689,670 | 8/1987 | Okazaki | 358/111 |
| 4,737,464 | 4/1988 | McConnell et al. | 436/43 |
| 4,769,776 | 9/1988 | Hiroaka et al. | 364/555 |
| 4,817,123 | 3/1989 | Sones et al. | 378/98 |

(List continued on next page.)

OTHER PUBLICATIONS

McGraw–Hill Encyclopedia of Science and Technology (13), 7th Edition, Published by McGraw–Hill, Inc., New York, (1997), pp. 411–421 (No Author).

McGraw–Hill Yearbook of Science and Technology (1997), Published by McGraw–Hill, New York. (No Author) (No Page Number).

*Primary Examiner*—Leo Boudreau
*Assistant Examiner*—Bijan Tadayon
*Attorney, Agent, or Firm*—Flehr Hohbach Test Albritton & Herbert, LLP

[57] ABSTRACT

A method and system for automatically analyzing the presence of an analyte in a liquid specimen of biological origin are described. The liquid specimen is added to a testing substrate that has a receptor immobilized on a portion of its surface. If analyte is present in the specimen, it will specifically bind to the receptor. A labeled reagent is added to the testing substrate which will bind to the analyte, if present, and generate a color on the testing substrate. The testing substrate is then illuminated and, using electronic equipment, a digital image of its surface is acquired and automatically scanned to locate an area that has the highest color density, which corresponds to the presence of labeled reagent. A measurement of color density, corresponding to pixels per unit area, is generated. An area peripheral to the area of highest color density, which represents background density, is also located and a measured. The presence or absence of analyte in the liquid sample is determined by adjusting the measurement of labeled reagent with the background density measurement in accordance with a predefined mathematical function. In some cases, the result of the test will be interpreted as a binary, positive/negative result according to whether the measurement taken is above or below a given threshold. In other cases, a continuous range of values may be generated from different samples that correspond to the concentration of the analyte present in each tested sample.

16 Claims, 5 Drawing Sheets

U.S. PATENT DOCUMENTS

| | | | |
|---|---|---|---|
| 4,850,029 | 7/1989 | Moyer et al. | 382/52 |
| 4,855,930 | 8/1989 | Chao et al. | 364/497 |
| 4,875,104 | 10/1989 | Kamon | 358/400 |
| 4,882,492 | 11/1989 | Schlager | 358/101 |
| 4,884,213 | 11/1989 | Iwata et al. | 364/498 |
| 4,891,757 | 1/1990 | Shroy et al. | 364/413.13 |
| 4,922,915 | 5/1990 | Arnold et al. | 128/653 R |
| 5,008,185 | 4/1991 | Bacus | 435/7.23 |
| 5,014,216 | 5/1991 | Stafford et al. | 364/496 |
| 5,018,209 | 5/1991 | Bacus | 382/6 |
| 5,121,338 | 6/1992 | Lodder | 364/498 |

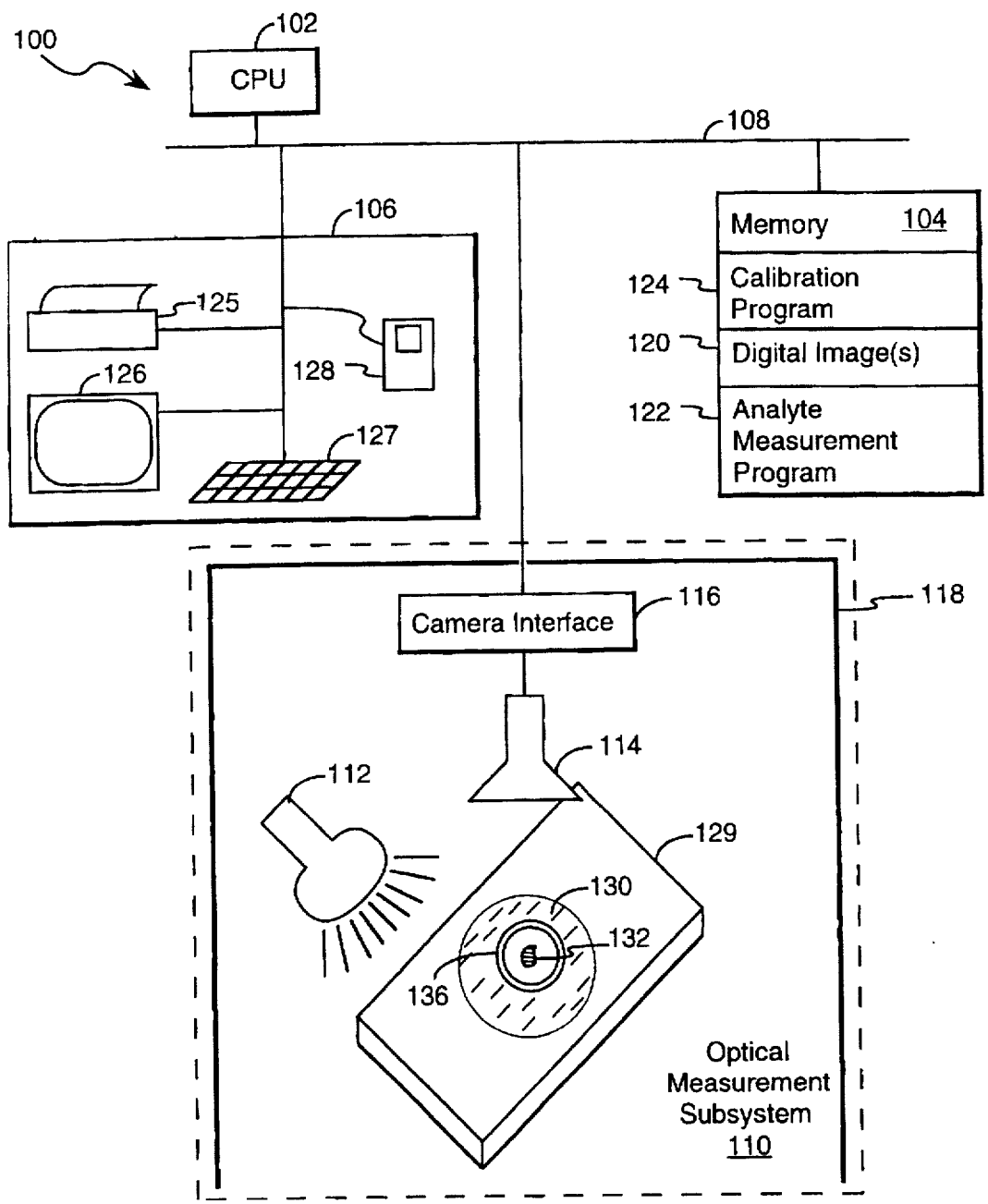
FIG._1
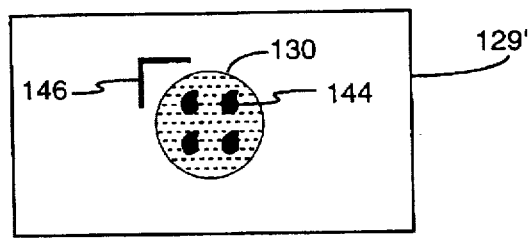
FIG._2

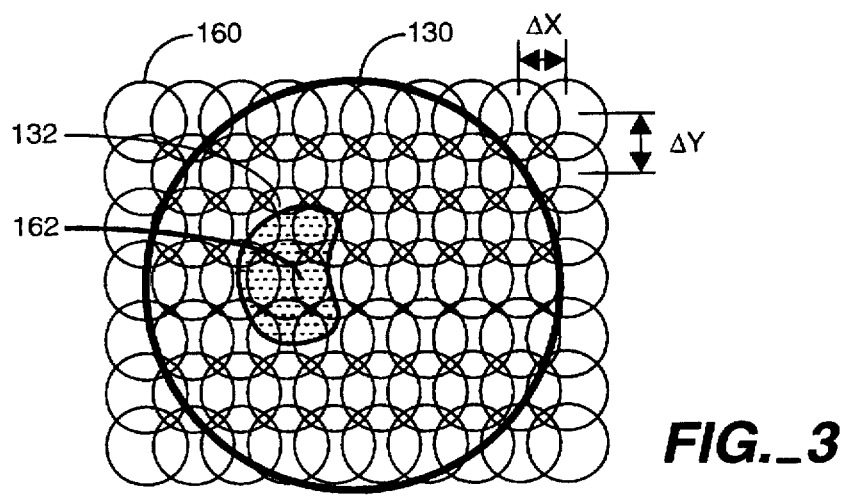
FIG._3
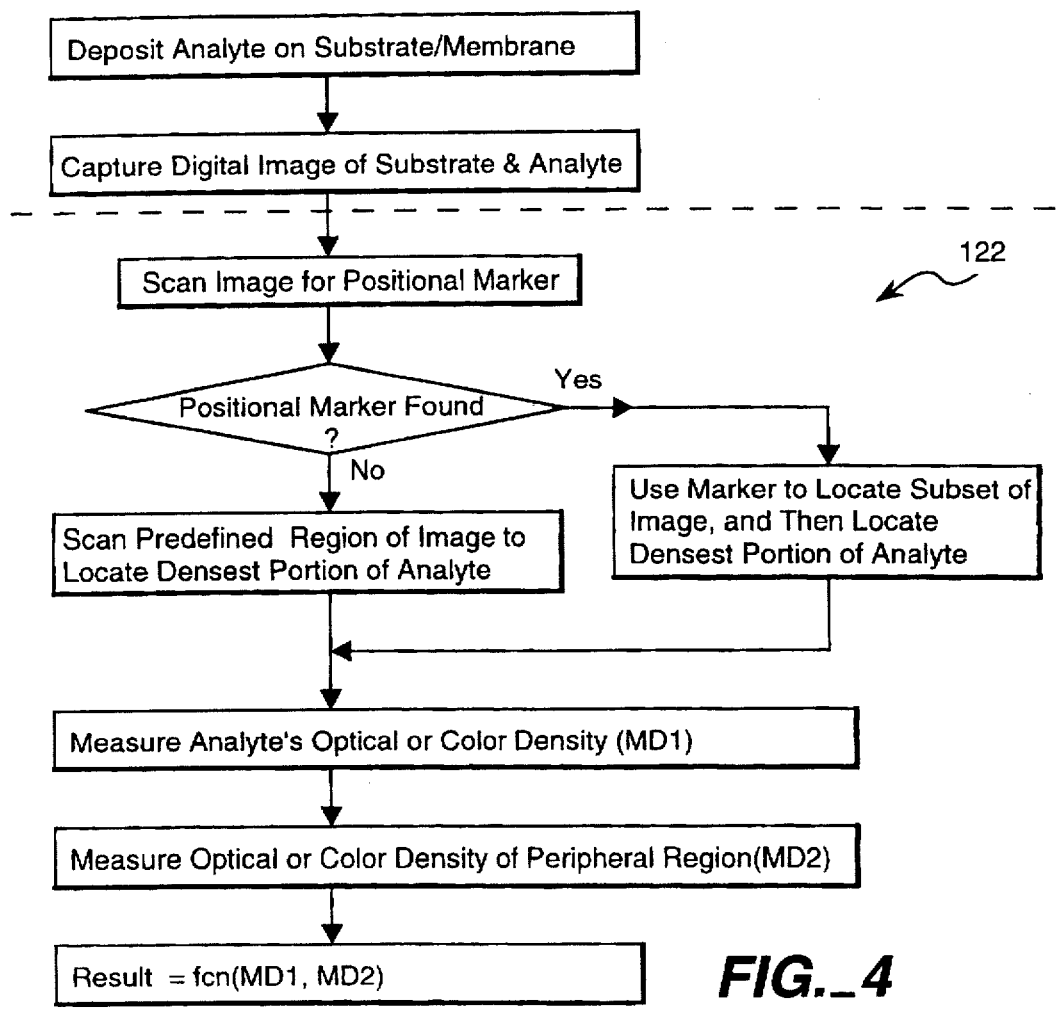
FIG._4

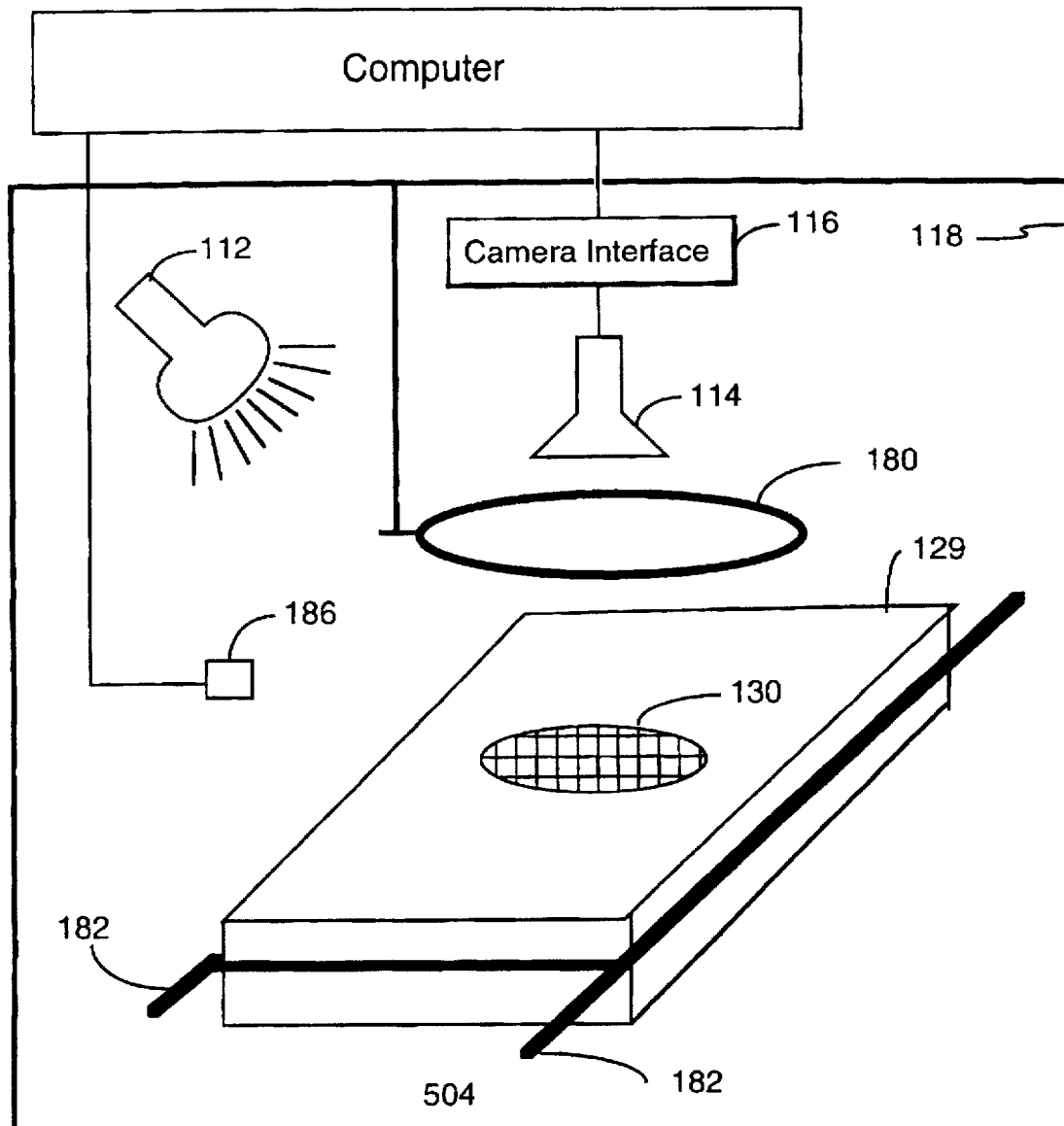
FIG._5

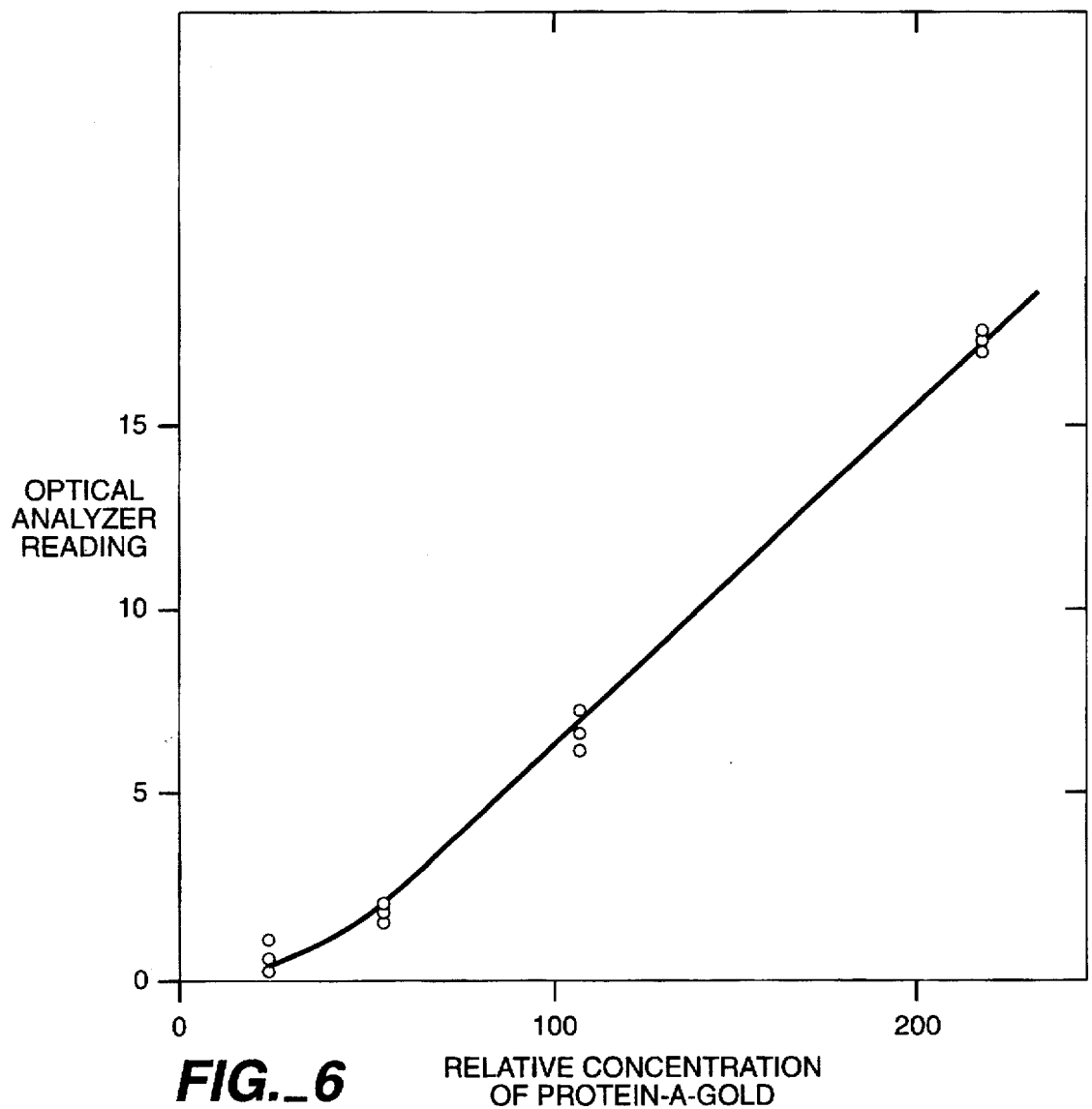
FIG._6

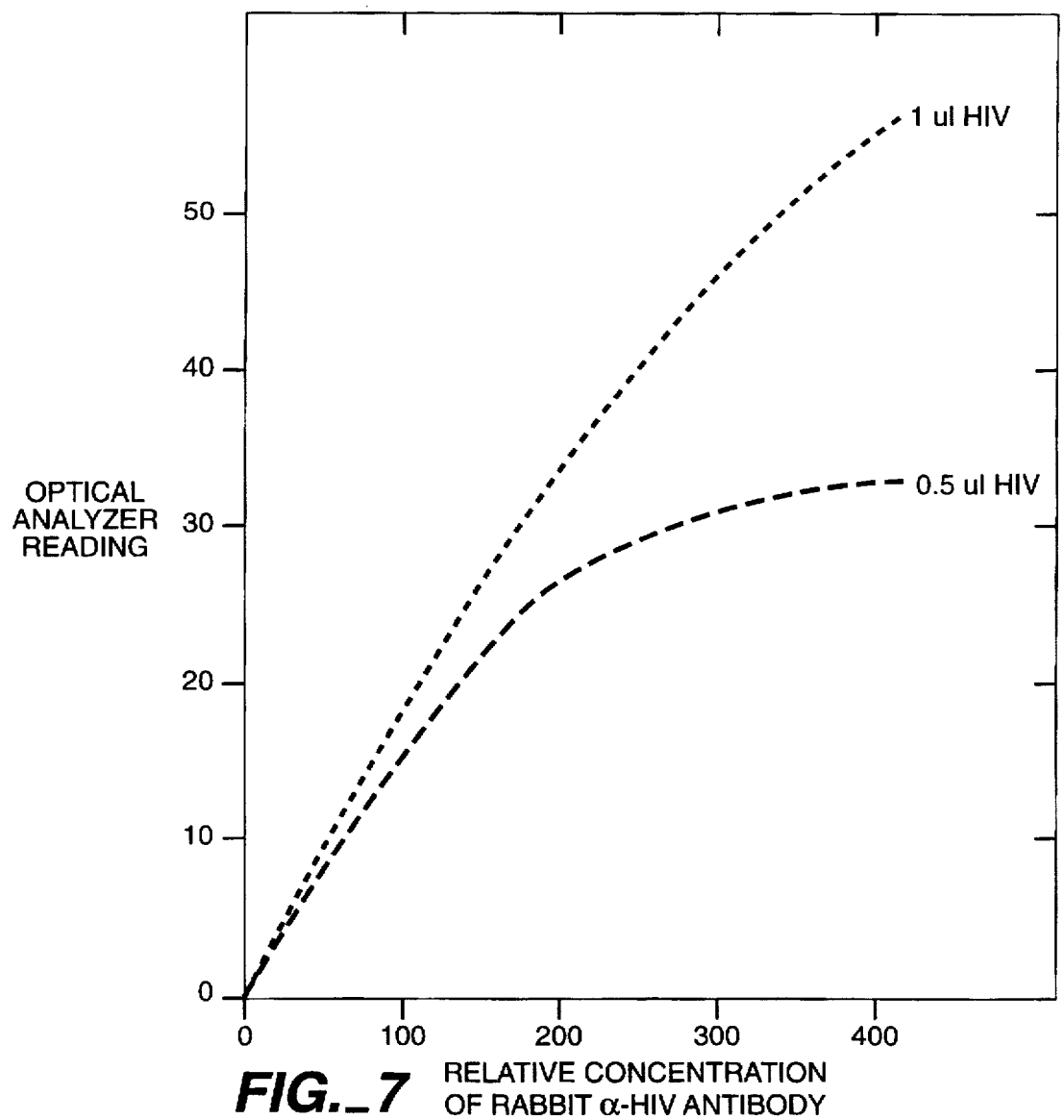
FIG._7 RELATIVE CONCENTRATION OF RABBIT α-HIV ANTIBODY

OPTICAL SPECIMEN ANALYSIS SYSTEM AND METHOD

REFERENCE TO RELATED APPLICATIONS

This is a continuation-in-part application of U.S. Ser. No. 08/023,113 filed Feb. 26, 1993, now abandoned.

FIELD OF INVENTION

The present invention relates generally to systems and methods of analyzing specimens, preferably specimens of biological origin, and particularly to computerized methods and systems for optical analysis of such specimens.

BACKGROUND OF THE INVENTION

Many laboratory tests are determined by how a particular analyte present in a sample reacts with a specific reagent. Often, these tests are qualitatively determined by visual inspection. For example, current home pregnancy tests can detect human chorionic gonadotropin (HCG), a hormone secreted in the urine of pregnant women. Typically, the urine is applied to a testing substrate that has an antibody immobilized thereon that is capable of binding to the HCG. A labelled reagent is then applied to the testing substrate that is capable of specifically binding to HCG, and thus, in the presence of HCG, will color the testing substrate, thus indicating a potential pregnancy. For such tests, the user can tell the results at a glance. However, with increasing demand for rapid diagnostic testing in a laboratory setting, visual inspection by a human technician becomes a bottleneck. In addition, human technicians are error prone, especially when performing diagnostic tests that require quantitative measurements of color or optical density. Furthermore, quantifying test results is very difficult for human technicians when the color density of the testing substrate varies due to differences in the amount of reagent used for each test, the amount of liquid (such as blood plasma) deposited on the substrate, or by different batches of reagents used in the test. Additionally, the results of such tests often depend on the difference in color saturation associated with a specific region of the testing substrate where the analyte specifically binds compared to another region of the testing substrate where the analyte is not supposed to bind and thus where the presence of color indicates the degree of "background" or "noise" in the test. This is particularly true for rapid immunoassays that use membranes as the testing substrates that have discrete zones having receptors immobilized thereon that specifically bind to the analyte present in the sample tested.

Consequently, a number of prior art systems have been designed to partially automate the process of quantifying test results. For example, the results of electrophoretic immunoblots (Western Blots), the main method for verification of human immunodeficiency virus seropositivity, can be quantitated using densitometry. Typically with a Western Blot, bands of electrophoresed proteins are transferred to a nitrocellulose strip and then incubated with patient sera. If antibodies specific to the proteins are present in the sera, they will bind to the blotted proteins. The presence of the antibodies can be detected using labelled antibodies to human IgG. If labels are used that generate a visible color, bands will appear that correspond to the location of the blotted proteins for which the patient has antibodies. The concentration of the antibodies can be quantitated using a densitometer, an instrument which measures optical density by measuring the intensity of reflected light. The nitrocellulose strip is passed through a beam of light, so that the intensity of each band is measured and a value is generated that correlates to the concentration of antibody present in the patient sera. However, the densitometer only measures one point of each band as opposed to scanning the entire area of the band. Because the color intensity of a band can vary, as well as the background color surrounding each band, the values generated by densitometry can vary and thus may not accurately reflect the true concentration of the substance being measured.

Reflectometers are also used to quantitate the results of certain laboratory tests, particularly, rapid immunoassays such as those described in U.S. Pat. Nos. 5,006,464 to Chu et al. and 4,632,901 to Valkirs et al., which, after the performance of assay steps, can result in the appearance of a colored region on a testing substrate to indicate the presence of a particular analyte in a sample. The reflectometer is a photoelectric instrument for measuring the optical reflectance of a surface. Typically, the rapid immunoassay comprises a testing substrate such as a porous membrane. A small portion of the testing substrate has a receptor immobilized thereon (i.e. the receptor area—usually a small circular area or dot) that is capable of binding directly or indirectly to an analyte such as an antibody, protein, hormone, or any other substance that is suspected of being present in a patient sample. Thus, when a patient sample, such as plasma or urine, comes in contact with the testing substrate, the analyte, if present in the sample, will bind specifically to the receptor area of the testing substrate, but not to the peripheral area of the testing substrate where no receptor is immobilized. The remainder of the sample and any unbound analyte will flow through the testing substrate, if it is porous, and/or can be washed off. A labeled reagent is added that is capable of binding directly or indirectly to the analyte to generate a colored dot or circle (or whatever shape the receptor area is). Thus, if the analyte is present in the patient sample, it will bind to the receptor area and its presence will be indicated by the generation of color after application of the labeled reagent.

The results of the immunoassay can then be measured using a reflectometer. Typically, the testing substrate needs to be inserted into the reflectometer so that the receptor area will align with a beam of light that is used to measure reflectance. Therefore, if the receptor area is not accurately positioned on the testing substrate, the results of the assay will not be accurately measured. Additionally, there may be variation in the color intensity generated at the receptor area. Thus, the beam of light may not line up with the part of the receptor area that most accurately correlates to the concentration of analyte present in the patient sample.

Digital analysis has been used in some testing procedures, but has not been used for quantifying the results of immunoassays. For example, U.S. Pat. No. 5,018,209 issued May 21, 1991 and U.S. Pat. No. 5,008,185 issued Apr. 16, 1991, both to Bacus, describe digital image processing methods and apparatus to analyze various features of cells being viewed on a slide under a microscope. Because the cells (or portions thereof) are randomly located on the slide, the technician and system work in an interactive fashion whereby the technician manually locates the cells on the slide that the system thereafter analyzes. Thus, while the efficiency of the testing process is increased by such an interactive system, it is not as efficient as one which would automatically locate the region of interest without human interaction.

U.S. Pat. No. 4,922,915 issued May 8, 1990 to Arnold, describes an automatic image location method in the field of medical imaging technology, such as computer tomography (CT) and magnetic resonance imaging (MRI). In a typical diagnostic scan of a patient, several reference samples of known optical density are placed in proximity with the patient's body and are scanned simultaneously. These images of the reference samples of known density are compared with the images of various regions of the patient's body to determine the relevant characteristics of those regions.

The method in Arnold is concerned with locating two regions: the reference samples and the regions of interest within the patient's body. With respect to the reference samples, the system locates the samples automatically by two separate algorithms. The first algorithm uses the fact that the reference samples are of known optical densities. The Arnold system searches the entire digital image for regions with these optical densities.

The second location algorithm uses pre-positioned metallic rods proximately placed to the reference samples. Initially, the system starts scanning the entire digital image for pixels of greatest density. These pixels correspond to the metallic rods. Once the rods are located, the reference samples are easily located because the orientation of the samples in relation to the metallic rods is predefined.

With respect to locating regions of interest in the patient's body, the search performed by the Arnold system is not fully automated. After the reference samples are located, Arnold requires that a human operator define an enlarged region of interest, for example around a bone structure, which the system thereafter refines. This step in Arnold is necessary because the system is unable to exclude regions which add error to the density readings.

While Arnold's method of automatically locating digital images works well when regions are either of known densities or known orientations, it is not satisfactory when the region of interest has neither known intensity or position. In Arnold's method, human interaction during the analysis step is always required.

The above-mentioned methods of digital analysis do not preform quantitative analyses of specimens, but rather only locate a region of interest based on optical density. However, in the analysis of chemical and biological specimens, it is often the density of a particular color that is the relevant measurement parameter. For instance, some immunoassays employ labeled reagents, such as certain colloidal reagents, that generate a color when an analyte is detected in a biological specimen.

Therefore, it is an object of the present invention to provide a system and method for automatic image location and quantitative analysis when the region of interest is of neither known intensity or position in the image.

Another object of the present invention is to provide a reliable automated method for quantifying the results of an immunoassay wherein the method provides a more accurate measurement that better corresponds to the true concentration of an analyte in a fluid sample compared with prior art methods that use densitometers and reflectometers.

SUMMARY OF THE INVENTION

In summary, the present invention is a method and system for the automatic analysis of a testing substrate for an analyte derived from a specimen, such as a specimen of biological origin, when neither the position nor the optical density (or color density) of the region of the testing substrate where the analyte, if present, is precisely known. The invention also provides a method for more accurately measuring the concentration of the analyte in the specimen.

The method comprises the steps of applying a liquid sample suspected of containing an analyte to a testing substrate having an immobilized thereon, in a limited region of the testing substrate, a receptor capable of directly or indirectly binding to the analyte. A labeled reagent, capable of binding directly or indirectly to the analyte and generating a color signal, is added to the testing substrate. If the analyte is present, a color is generated at the area of the testing substrate where the receptor is immobilized.

The testing substrate is then illuminated and, using electronic equipment, a digital image of the testing substrate is acquired. In preferred embodiments, the testing substrate is illuminated using reflected light. The illumination is pre-calibrated to correct for lighting intensity variations. The digital image is automatically scanned to locate an area of the testing substrate having the highest color density and generating a first measurement of color density that corresponds to pixels per unit area. To aid in the scanning of the digital image, one embodiment of the invention employs a positional marker on the substrate (such as a dark or colored circle, line, spot, or any other shape) to generally indicate where the immobilized receptor is located. The use of a positional marker reduces both the amount of time require to locate the receptor area and the degree of error in locating the most optically dense portion of the testing substrate.

Next, an area peripheral to the area of highest color density is located and a second measurement of color density is generated that corresponds to pixels per unit area. Because this peripheral area is not proximate to the receptor area where the analyte, if present in the sample, specifically binds, this area represents the background density of the substrate, which can be considered to be the background "noise" in the measurement of the analyte. In a preferred embodiment, the second measurement is generated that corresponds to the pixels per unit area in an annular region that circumscribes the receptor area. The presence or absence of the analyte in the liquid sample is calculated by adjusting the first measurement with said second measurement in accordance with a predefined mathematical function.

In some cases, the result of the test will be interpreted as a binary, positive/negative result according to whether the measurement taken is above or below a given threshold. In other cases, a continuous range of values may be generated from different samples that correspond to the concentration of the analyte present in each tested sample.

BRIEF DESCRIPTION OF THE DRAWINGS

Additional objects and features of the invention will be more readily apparent from the following detailed description and appended claims when taken in conjunction with the drawings, in which:

FIG. 1 is a block diagram of a system for optically analyzing biological and other analytes.

FIG. 2 shows a sample holder with multiple analytes deposited thereon.

FIG. 3 is a conceptual diagram of the method used to locate the optically densest portion of an analyte deposited on a substrate.

FIG. 4 is a flow chart of the steps of the present invention.

FIG. 5 is a block diagram of an alternate embodiment of a system for analyzing biological and other analytes.

FIG. 6 shows the linear titration curve obtained using the optical analyzer.

FIG. 7 shows relationship between linearity of titration curve and amount of receptor bound to testing substrate.

DESCRIPTION OF THE PREFERRED EMBODIMENT

The method aspect of the invention involves the analysis and measurement of assay results for the determination of the presence or absence of an analyte in a sample, preferably a sample of biological origin. The type of assay that is performed prior to the measurement step can be one of many assays known in the art as long as the assay employs a testing substrate that has a limited area to which the analyte is concentrated, and a peripheral area to which the analyte does not specifically bind. In a preferred embodiment, the assay is an immunoassay for the detection of an analyte in a biological sample wherein the testing substrate is a liquid-permeable membrane which has a receptor bound on a limited area thereof. The receptor is capable of specifically binding to the analyte. This type of immunoassay is well known by those skilled in the art and is described in further detail in U.S. Pat. No. 5,006,464 to Chu et al., incorporated herein by reference.

In general, the analyte can be any substance that may be present in a liquid sample that is to be detected by the assay procedure. In preferred embodiments, the liquid sample is of biological origin, such as urine, plasma, serum, whole blood, and the like. The liquid sample may also comprise a diluent to which the contents of a throat swab, vaginal swab, bacterial culture, or other biological specimen has been added. Thus, in a preferred embodiment, the analyte may be a "biological analyte", that is any substance present in a biological sample that is sought to be detected. For example, the analyte may be an antibody to a particular virus, such as the Human Immunodeficiency Virus (HIV), Rubella, Herpes Simplex Virus I and II (HSV I and HSV II), etc.; a bacteria such as *Streptococcus pyogenes* or *Neisseria gonorrhea*; a hormone such as human chorionic gonadotropin (HCG) or luteinizing hormone; a protein, or any other detectable substance that may be present in a biological sample. Numerous other possible analytes are listed in U.S. Pat. No. 5,006,464 to Chu et al. Additionally, the assay may test for the presence of more than one analyte. Thus, the term "analyte" generally refers to one or more a specific type of substance that is present in a sample. For example, in the case of an assay for the diagnosis of pregnancy, the analyte is HCG. However, numerous HCG molecules would be present in the serum or urine sample of the patient. The term "analytes" or "more than one analyte" refers to more than one specific type of substance in a sample. For example, an assay that detects the presence of HSV I and HSV II is an assay that detects the presence of more than one analyte (i.e two different analytes).

The liquid sample is applied to a testing substrate. Any testing substrate can be used as long a receptor that is capable of binding to the analyte can be immobilized onto the testing substrate. Thus, the testing substrate can be a porous or a non-porous surface. In a preferred embodiment, the testing substrate is a porous surface such as a fiberglass or nitrocellulose membrane through which the liquid sample can flow. Typically, the testing substrate is an exposed surface of an immunoassay device such as the device described in U.S. Pat. No. 5,006,464 to Chu et al. Other suitable immunoassay devices that employ porous testing substrates are well known in the art.

A limited region of the testing substrate has a receptor immobilized thereon that is capable of directly or indirectly binding to the analyte. This region, which may take any shape, but which is typically a small circle or dot, is hereinafter termed the "receptor area". If a second analyte is to be tested simultaneously, then there is a second receptor area on the substrate that is separate and distinct from the first receptor area. By way of example, if the analyte is a human antibody to HIV, the receptor may be an HIV antigen. The HIV antigen is immobilized onto a portion of the testing substrate using known methods. If antibody to HIV is present in the liquid sample, it will specifically bind to the HIV antigen. The remainder of the testing substrate will not specifically bind to the antibody. Thus, after the liquid sample is applied to the testing substrate, the analyte, if present in the sample, will be concentrated at the receptor area.

A labeled reagent, capable of binding directly or indirectly to the analyte and generating a color signal, is added to the testing substrate. If more than one analyte is being tested simultaneously, more than one labeled reagent is added to the testing substrate, either simultaneously or sequentially. The term "capable of binding directly", means that the labeled reagents can specifically bind to the respective analytes. For example, if the analyte is a human IgG, the labelled reagent may be labelled antibody to human IgG, or labelled protein A, which binds to the FC fragment of IgG. The term "binding indirectly" means that at least one intermediate reagent is added to the testing substrate that is capable of binding to the analyte, and the labeled reagent is capable of binding to the intermediate reagent. For example, if the analyte is human IgG, an intermediate reagent may be a rabbit antibody to human IgG. The labelled reagent may be a goat antibody that specifically binds to the rabbit antibody.

The presence of bound analyte is indicated by the presence of color that is generated by the labeled reagent. The label may be a colored substance itself, such as colloidal gold which, when concentrated at the receptor area, generates a red color. Alternatively, the label may be an enzyme which, when substrate for the enzyme is added, causes a colored product to be generated. A variety of labels are well known in the art. Techniques are well-known in the art for attaching labels to reagents. A preferred embodiment of the invention employs a reagent labelled which colloidal gold because an enzyme-substrate reaction is not required to generate color, thus requiring fewer steps in performing the assay, and high sensitivity can be achieved using colloidal labels.

In order to measure the results of the assay, the testing substrate is illuminated and, using electronic equipment, a digital image of the testing substrate is acquired. In preferred embodiments, the testing substrate is illuminated using reflected light. The illumination is pre-calibrated to correct for lighting intensity variations. The digital image is automatically scanned to locate an area of the testing substrate having the highest color density, i.e. the highest number of pixels per unit area, and generating a first measurement of color density. To aid in the scanning of the digital image, one embodiment of the invention employs a positional marker on the substrate (such as a dark or colored circle, line, spot, or any other shape) to generally indicate where the immobilized receptor is located. Once the general region for the immobilized receptor is identified, the region will be identified for the area having highest color density. The use of a positional marker reduces both the amount of time require to locate the receptor area and the degree of error in locating the most optically dense portion of the testing substrate.

Next, an area peripheral to the area of highest color density is located and a second measurement of color density is generated as determined by the number of pixels per unit area. Because this peripheral area does not include any portion of the receptor area (where the analyte, if present in the sample, specifically binds) its measurement represents the background density of the substrate and thus the "noise" in the measurement of the analyte. Background color may result from non-specific binding of the analyte or labeled reagent to areas of the testing substrate where there is no receptor bound. If the assay is done properly, the background color should be much less than the color generated at the receptor area when analyte is present in the sample. However, in some cases, even when assay procedures are done properly, portions of the peripheral area can be as dark as the area where analyte has bound specifically to receptor. This can sometimes happen if the biological sample being tested has particulate matter that is trapped by the membrane and unable to flow through. Samples that have been frozen and thawed often contain particulate matter that can lead to background problems.

High levels of background can also occur if the substrate is not even and, as a result, aggregates in the sample pool at a particular region of the substrate. In prior art immunoassay methods that employ refractometers, a positive sample that produces high background can be falsely diagnosed as negative if the area of high background on the testing substrate coincides with the point where background reflectance is measured. Because the present invention uses digital technology to determine the number of pixels per unit area, a larger area of background can be measured, not just one point as with reflectance, and thus a more accurate reading can be obtained than is possible with prior art technologies. In a preferred embodiment the background density is determined by measuring an annular region that surrounds the receptor area is measured. If there is more than one receptor area, two annular regions, one for each receptor area, would be measured. Alternatively, a single large background region could be defined for all receptor areas. The preferred approach for background determination may vary depending upon the size of the receptor areas, the type of sample to be tested and the nature of the flow of the sample.

After the region of highest color density (first measurement) and background density (second measurement) are determined, the presence or absence of the analyte in the liquid sample is calculated by adjusting the first measurement with the second measurement in accordance with a predefined mathematical function as exemplified in more detail below. If a positional marker is used that is located within the peripheral area, then the second measurement is adjusted so that the color intensity of the positional marker is not included as part of the background measurement. Because color intensity can sometimes vary depending upon whether the testing substrate is wet or dry, the first and second measurements can also be adjusted to take into consideration this factor. For example, calibration spots on the testing substrate could be used that have a fixed color intensity, independent of the sample being analyzed, but dependent on whether the testing substrate is wet or dry. The calibration spot could also serve a dual purpose as a positional marker.

The result of the test can be interpreted as a binary, positive/negative result according to whether the measurement taken is above or below a given threshold. In preferred embodiments, the adjusted measurement, which corresponds to an adjusted number of pixels per unit area, will be quantitative, correlating to the concentration of analyte present in the sample. Typically, for quantitative measurements, a standard calibration curve of a known sample would be generated and used to determine the concentration of the sample tested based on the measurements generated from the test sample.

In describing the system aspect of the present invention, reference is made to FIG. 1, where there is shown a block diagram of the system for optically analyzing biological and other analytes designed in accordance with the principles of the present invention. System 100 includes a central processing unit (CPU) 102, computer memory 104, user interface 106, system communication bus 108, and an optical measurement subsystem 110. The optical measurement subsystem 110 includes a shadowless (i.e., uniform) light source 112, camera 114, and camera interface 116. The optical measurement subsystem 110 is typically enclosed in a housing 118 so that optical images of analytes can be obtained under controlled optical conditions.

Memory 104, which will typically include both random access memory and secondary memory such as magnetic disk storage mechanisms, is sufficiently large enough to store a plurality of digital images 120, analyte measurement program 122, and a light source calibration program 124. Alternatively, programs 122 and 124 could be stored on Read Only Memory (ROM) chips.

It should be noted that the specific memory devices used are not important to the operation of the present invention so long as they have sufficient capacity and operating speed to enable the optical image analysis tasks described below.

The user interface 106 will typically include at least one output communication device such as a printer 125 and/or monitor 126 for communicating the results of tests conducted by the system, and at least one input communication device such as keyboard 127 and/or mouse pointer device 128. Many other combinations of user interfaces could be used, and the specific interfaces shown in FIG. 1 should not be construed as a limitation.

Before any testing substrates are analyzed, light source 112 is calibrated. Calibration is performed each time the system is powered on, and may need to be performed periodically if the system is kept on for long periods of time, because any changes in the light source's intensity could affect the result of the test. For example, if the measurement produced by the test is greater than a certain threshold value, the result of the test may be deemed positive. Otherwise, the test may be negative. These threshold values, stored as constants (or as a mathematical formula) in the analyte measurement program 112, are based upon a certain light intensity level. Without proper calibration, the possibility of false test results increases.

In the preferred embodiment, calibration is accomplished by calibration program 124 by measuring the light source's intensity with a light sensor (see light sensor 186 in FIG. 5). In an alternate embodiment of the invention, the calibration program 124 takes as input an image of a calibration substrate. In the preferred embodiment a calibration substrate is a regular testing substrate without any analyte deposited on its surface. The intensity of light is measured according to the average density of the image of the calibration substrate. Then, a calibration coefficient is computed by dividing the average image density with a predefined standard value. All subsequent image density values are multiplied by this calibration coefficient.

When system 100 is ready for operation, camera 114 takes an analog image of at least a portion of the top surface of test carrier 129. The top surface of carrier 129, as depicted in FIG. 1, includes testing substrate 130 on which is deposited a chemically active reagent. Prior to insertion of carrier into the optical measurement subsystem 110, an analyte 132, typically derived from a biological specimen, is deposited onto the region of the test carrier where substrate 130 is located. In the preferred embodiment, the chemical interaction of the analytes 132 with the chemically active substrate 130 typically causes the analyte 132 to be the optically densest portion of the substrate 130.

FIG. 2 shows a test carrier 129' with multiple analytes 144 deposited on its substrate 130. Positional marker 146 gives the relative position of substrate 130 on carrier 129'. As previously mentioned, marker 146 may be any shape or size sufficient to indicate the general position or location of the substrate 130 and/or the analyte(s) on the test carrier 129'.

The analog image generated by camera 114 is digitized by camera interface 116 and sent via bus 108 to memory 104 where the digital image is stored as an array of pixel values. In the presently preferred embodiment, the portion of the test carrier 129 captured by the camera 114 is 5/16"×5/16" and is represented as a 170×170 array of pixel elements. Additionally, the presently preferred embodiment has the capability to process both color and gray scale images, with 8-bit pixels (256 gray scale levels) being used for gray scale images and 24-bit pixels ($256^3$ levels) being used for color images. It should be appreciated that the image could be formed from more or less pixel elements and more or less scale image levels to alter the image resolution and sensitivity. It will also be appreciated that other data structures for image storage are possible.

Note that for some analyte measurement tests the measured "density" of the analyte and background regions of the digital image will be the total optical density of a portion of the digital image, while for other analyte measurement tests the measured density will be the density of a particular color. That is, when the digital image is a color image each pixel will be represented by Red, Green and Blue (RGB) values, and the test measurements can be based on any one or predefined combination of the three RGB color values for the image's pixels. Thus, the term "density" in the discussions below concerns the density of a preselected optical characteristic of the digital image which is relevant to the measurement being performed.

After the digital image has been captured, the image is analyzed by analyte measurement program 122. This analysis includes locating the analyte by locating within the digitized image a circular region of predefined size having the greatest optical density, locating a "background" region of the substrate 130 that is not covered by the analyte, and computing a test result by computing a predefined mathematical function of the average density of the background region and the average density of analyte region. The mathematical function may be as simple as subtracting the background density from the analyte density, or may be a considerable more complex function. In the preferred embodiment, the circular region of greatest optical density is sized to be small enough so as to be entirely covered the smallest anticipated analyte, and thus the average optical density of the circular region should be representative of the optical density of the chemically reacted analyte.

To accomplish this analysis, analyte measurement program 122 performs three main processes: pre-scan, fine-scan, and background density compensation. It will be appreciated that program 122 executes differently according to whether a positional marker is included on the test carrier 129 or not. Program 122 takes the digital image stored in memory 104 as input and begins a raster scan of the entire image. If a positional marker is present, program 122 then performs a raster scan across the image to locate the marker, which will typically be either the pixels of greatest density, or pixels of a particular color. From the orientation of the marker, program 122 will determine a smaller region of interest. Thereafter, program 122 confines its pre-scan and fine-scan processes to this defined region. If no positional marker is present on the substrate, then program 122 executes its pre-scan and fine-scan processes on a predefined region of the digital image.

The pre-scan process searches the region of interest for an area of greatest average density. This area will correspond to the reaction of the analyte to the reagent. The area should be as large as possible while still fitting entirely within the site of the analyte and should be sufficiently small to avoid noise sensitivity. In the preferred embodiment, the portion of the digital image used to determine the optical density of the analyte is a circle of diameter 64 pixels across.

FIG. 3 is a conceptual diagram of the pre-scan process used to approximately locate the densest area of the analyte 132 deposited on the substrate 130. Please note that FIG. 3 is not drawn to scale, and that the analyte 132 will typically cover a much smaller fraction of the substrate 130 than shown in this conceptual representation of the scanning process. The pre-scan process measures and compares the densities of a sequence of circular regions 160 arranged in columns and rows, where the centers of the columns are spaced apart by a distance of $\Delta X$ and the centers of the rows are spaced apart by a distance of $\Delta Y$. By comparing the densities of these regions the prescan process determines center of the circular region 160 of greatest density, as represented by circular region 162, and thereby locates the approximate center of the analyte. Table 1 contains a pseudocode representation of this process.

TABLE 1

PRESCAN PROCESS

-- Specify range of regions to be tested:
  X1, Y1 = center of top-left region to be tested
  X2, Y2 = center of bottom-right region to be tested
-- CX, CY and CD represent the position and density
-- of the region of greatest optical density found so far.
  CX = X1
  CY = Y1
  CD = 0
  For X = X1 to X2, by steps of size $\Delta X$
  {   For Y = Y1 to X2, by steps of size $\Delta Y$
    {   Measure density D of region centered at X,Y within a
        radius of Z pixels
      -- Update center value whenever higher density region
      -- is found
        If D > CD
        {   CX = X
            CY = Y
            CD = D
        }
    }
  }

After the region of greatest optical density is approximately found, the fine-scan process is used to more precisely locate the reaction region of greatest optical density. The fine-scan process takes as its input the center of the area of greatest density obtained from the prescan process. The center of the area is then shifted by one or two pixel elements in both the X and Y coordinates. The densities of these resulting areas are then calculated by summing the pixel element readings for the areas. The measured optical or color density for each area is compared with the greatest density located by the pre-scan process, and the greatest density area is accordingly updated. The fine-scan process then computes the average pixel density for the area by taking the greatest density reading and dividing by the number of pixels in the circle. This average density is the output result of the fine-scan procedure. Table 2 contains a pseudocode representation of this process.

TABLE 2

FINE-SCAN PROCESS

- - Initialize the starting X and Y ranges from the
- - center of the region found in Prescan.
  X_START = CX
  Y_START = CY
- - Let S1, S2, S3, S4, S5 and S6 be relatively small
- - integer values greater than zero.
  For X = X_START − S1 to X_START + S2, by steps of S3
  { For Y = Y_START − S4 TO Y_START + S5, by steps of S6
     {  Measure density D of region centered at X,Y
        within a radius of Z pixels.
        - - Update center value whenever higher
        - - density region is found.
        If D > CD
        {   CX = X
            CY = Y
            CD = D
        }
     }
  }

After the fine-scan process refines the center coordinates of the region of greatest density, the analyte measurement program 122 then performs a background compensation step. To obtain the necessary background reading, annular region 136, as shown in FIG. 1, is selected by program 122. Annular region 136 has an inner radius sufficiently large such that none of the analyte 132 is found in region 136. An average pixel density for annular region 136 is computed as discussed above. The measured density of the analyte is then adjusted in accordance with the measurement background region density. In some cases the adjustment is simply a subtraction operation, while in others it may be accomplished by division or other mathematical operation.

This adjusted measurement value may be interpreted as the result of the test according to the nature of the reaction of the analyte with the reagent. In some cases, a simple threshold test will result. That is, if the adjusted measurement value is greater than a pre-determined threshold, then the test is considered positive. Otherwise, the test is considered negative. Alternatively, the adjusted measurement value may be a value in a continuous range of values that is to be interpreted by the user, or that is mapped with respect to a predefined scale and then presented for interpretation by the user. Thus, the adjusted measurement value may correspond to concentration of analyte present in the sample.

The flow chart in FIG. 4 represents the sequence of steps used to test an analyte, from depositing the analyte onto the substrate through generation of the final measurement value.

An alternate embodiment of the present invention is depicted in FIG. 5. Instead of a positional marker being affixed to individual carriers, as shown as marker 146 in FIG. 2, a separate template 180 is positioned between camera 114 and carrier 129. The image of template 180 is thus superimposed upon the image of carrier 129 when the image is captured. To insure the proper alignment of the two images, template 180 would remain in a fixed location; while carrier 129 would be slid into position by way of guide rails 182. The image of template 180 would be used to mark the region where the analyte is deposited on the substrate. Use of the template would obviate the need to place position markers on individual carriers.

Also depicted in FIG. 5, a light sensor 186 can be positioned inside the measurement subsystem's housing 118 to measure the intensity of light emitted from light source 112. In this embodiment, readings from sensor 186 are used to calibrate the light source. This makes the calibration process totally automatic and thus the user is not required to perform or assist with the calibration process.

It will be appreciated that, although the presently preferred embodiment is currently used for the detection of antibodies to the human immunodeficiency virus (HIV), that application area is one of many potential applications and should not be construed as a limitation. In fact, the method and system of the present invention is broad enough to include the automatic testing of any analyte that visually reacts with any reagent.

It will further be appreciated that the present invention overcomes problems in prior automated systems. Specifically, the present invention does not require a human operator to work interactively at the analysis phase with the system to indicate the regions of interest for testing. Likewise, the present invention is able to locate the specific regions of interest without precisely knowing in advance either their location or their optical densities on the digital image.

EXAMPLE 1

Generation of Standard Curve

The exposed membrane of an immunoassay testing device was pretreated with a 1:10 dilution of normal human serum in phosphate buffered saline and dried. Protein A-colloidal gold at concentrations of 14.2 ng/µl, 7.12 ng/µl, 3.56 ng/µl and 1.78 ng/µl was inoculated onto the pretreated membranes in triplicate (i.e. 3 separate devices for each concentration). The digital readings generated by the colloidal gold was measured using the optical analyzer system described herein. The results were tabulated and plotted and are shown in FIG. 6. The results demonstrate that the reading obtained from the optical analyzer is concentration dependent. Thus, a measurement obtained from a sample having an unknown concentration of analyte can be compared to this type of standard curve to generate quantitative results.

EXAMPLE 2

Effect of Concentration of Antigen on Testing Substrate

Recombinant rabbit-anti-HIV recombinant protein antiserum (RbαHIV), having a concentration of approximately 125 µg/ml, was diluted with normal human serum using 2× serial dilutions. The diluted RbαHIV samples were added to the membranes of immunoassay devices having either 0.5 µl or 1.0 µl HIV recombinant antigen inoculated at the receptor area. A Protein A-colloidal gold conjugate was added to each immunoassay device. Measurements were obtained for each dilution of RbαHIV using the optical analyzer described herein. The results were tabulated and plotted and are shown in FIG. 7. The results demonstrate that at low concentration of analyte (RbαHIV) there is not much difference between the low (0.5 µl/membrane) and high (1.0 µl/membrane) concentrations of antigen at the receptor area. However, at higher concentrations of analyte, sensitivity increases with increased concentration of antigen at the receptor area. Standard curves like this can be prepared so that values from test samples can be compared with values of samples having known concentrations to generate quantitative information about the test sample. Standard curves can also be generated from known samples that have been assayed and allowed to dry onto the testing substrate prior to measurement, thus correcting for variation in measurements that can occur between wet and dry testing substrates.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A method for determining the presence of at least one biological analyte that may be present in a liquid sample comprising:

a) applying said liquid sample to a testing substrate having at least one receptor immobilized thereon at a first receptor area of said testing substrate, said at least one receptor being capable of specifically binding directly or indirectly to said at least one biological analyte, said first receptor area being located in a limited region of said testing substrate;

b) applying to said testing substrate a reagent that is capable of specifically binding directly or indirectly to said at least one biological analyte and capable of generating a color at said first receptor area when said at least one biological analyte is present;

c) illuminating said testing substrate and acquiring a digital image of said testing substrate;

d) using data processing equipment,
      (i) automatically scanning said digital image to locate an optically densest portion of said first receptor area and generating a first measurement of the density of said densest portion;
      (ii) locating an area peripheral to said first receptor area and generating a second measurement of background density of said area peripheral to said first receptor area; and
      (iii) generating an output signal by adjusting said first measurement with said second measurement in accordance with a predefined mathematical function in order to generate an output signal that indicates whether said at least one biological analyte is present in said liquid sample.

2. The method of claim 1 wherein said method is also used for the determination of a second biological analyte, said testing substrate having a second receptor immobilized thereon at a second receptor area, said second receptor area being capable of specifically binding directly or indirectly to said second biological analyte, said step (d) including locating and measuring the density of said first receptor area and said second receptor area and generating an output signal for said first receptor area and said second receptor area.

3. The method of claim 1 wherein the output signal of step (d)(iii) corresponds to the concentration of said at least one biological analyte present in said liquid sample.

4. The method of claim 1 wherein said testing substrate is a porous membrane.

5. The method of claim 1, wherein said testing substrate is opaque and includes a marker having a predefined spatial relationship to said first receptor area; said step (d)(i) including locating said marker in said digital image and then locating said first receptor area in said digital image based on said marker's location.

6. The method of claim 1, further including:

prior to step (d), measuring the optical density of a reference substrate and calibrating all subsequent measurements of testing substrates in accordance with said reference substrate's measured optical density.

7. The method of claim 1, wherein said digital image comprises an N×M array of pixels; said step (d)(i) including:
   (1) for each of a selected set of pixel positions spaced apart from each other, measuring the optical density of a region of said digital image associated with said each pixel position; (2) selecting a plurality of said regions measured in step (d)(i)(1) with highest density, (3) interpolating the pixel positions associated with said plurality of regions selected in step (d)(i)(2) to generate a final pixel position, and (4) measuring the optical density of a region of said digital image associated with said final pixel position to generate said first measurement.

8. A method for determining the presence of an analyte that may be present in a liquid sample comprising:

a) applying said liquid sample to a testing substrate having a receptor immobilized thereon at a receptor area of said testing substrate, said receptor capable of directly or indirectly binding to said analyte, said receptor area being located in a limited region of said testing substrate;

b) applying to said testing substrate a reagent capable of binding directly or indirectly to said analyte and capable of generating a color at said receptor area when said analyte is present;

c) illuminating said testing substrate and acquiring a digital image of said testing substrate;

d) using data processing equipment,
      (i) automatically scanning said digital image to locate a portion of said receptor area having greatest density of a predefined color, and generating a first measurement of the density of said predefined color at said located portion;
      (ii) locating an area peripheral to said receptor area and generating a second measurement of background density of said predefined color at said area peripheral to said receptor area; and
      (iii) generating an output signal by adjusting said first measurement with said second measurement in accordance with a predefined mathematical function in order to generate an output signal that indicates whether said analyte is present in said liquid sample.

9. The method of claim 8 wherein said method is for the determination of more than one analyte, said testing substrate having immobilized thereon more than one receptor area wherein each receptor area is capable of binding directly or indirectly to a specific analyte, said step (d) including locating and measuring the density of said predefined color at each receptor area, and generating an output signal for each receptor area.

10. The method of claim 8 wherein the adjusted measurement of step (d)(iii) corresponds to the concentration of analyte present in said sample.

11. The method of claim 8 wherein said testing substrate is a porous membrane.

12. A system for analyzing at least one analyte derived from a biological specimen, wherein said at least one analyte is bound to a first distinct receptor area of testing substrate wherein a portion of said testing substrate is not covered by said first distinct receptor area, said system comprising:

means for acquiring a digital image of said testing substrate; and data processing means, coupled to said image acquiring means, for automatically scanning said digital image to locate an optically densest portion of said digital image depicting said at least one analyte and to locate a background portion of said digital image not depicting said at least one analyte;

said data processing means including means for (A) generating a first measurement of the density of said densest portion, (B) generating a second measurement of the density of said background portion of said testing substrate, and (C) generating an output signal by adjusting said first measurement with said second measurement in accordance with a predefined mathematical function.

13. The system, as defined in claim 12, further including:

means of illuminating said testing substrate; and means for sensing the intensity of said means for illumination;

said data processing means including means, coupled to said intensity sensing means, for calibrating said measurements in accordance with said sensed intensity of said means for illumination.

14. The system, as defined in claim 12, wherein:

a multiplicity of distinct analytes are bound to a multiplicity of distinct receptor areas of said testing substrate;

said data processing means including means for locating an optically densest portion of each said distinct analyte, and for generating a first measurement of density of said optically densest portion of each said distinct analyte.

15. The system, as defined in claim 12, wherein said testing substrate includes a marker having a predefined spatial relationship to said at least one analyte; and said data processing means includes means for locating said marker in said digital image and for locating said at least one analyte within said digital image based on said marker's location.

16. The system, as defined in claim 12, further including:

a template interposed between said testing substrate and said means for acquiring a digital image, said template forming a superimposed image on said digitized image of said testing substrate;

a plurality of guide rails sized to receive said testing substrate so that said image of said template falls at predefined position with respect to said testing substrate, thereby indicating where said analyte is deposited on said testing substrate.

* * * * *